United States Patent [19]

Ivanov et al.

[11] Patent Number: 5,774,425
[45] Date of Patent: Jun. 30, 1998

[54] TIME MONITORING APPLIANCE

[75] Inventors: Andre Ivanov, Richmond; Alan Arthur Lowe, Vancouver, both of Canada

[73] Assignee: The University of British Columbia, Vancouver, Canada

[21] Appl. No.: 749,686

[22] Filed: Nov. 15, 1996

[51] Int. Cl.[6] .............................. G04B 47/00; G04F 8/00; G01K 1/02
[52] U.S. Cl. .............................. 368/11; 368/113; 374/102; 433/6
[58] Field of Search ........................ 368/10, 11, 107–113; 340/585, 588, 309.15, 691

[56] References Cited

U.S. PATENT DOCUMENTS

| | | |
|---|---|---|
| 3,885,310 | 5/1975 | Northcutt . |
| 3,906,797 | 9/1975 | Turner .................................. 73/362 R |
| 4,602,871 | 7/1986 | Hanaoka ................................ 374/102 |
| 5,245,592 | 9/1993 | Kuemmel et al. . |
| 5,262,758 | 11/1993 | Nam et al. .............................. 340/588 |
| 5,332,315 | 7/1994 | Baker et al. ............................ 374/102 |
| 5,341,291 | 8/1994 | Roizen et al. ...................... 364/413.02 |
| 5,464,044 | 11/1995 | Brinkerhoff ............................ 137/78.3 |
| 5,571,007 | 11/1996 | Ishiguro et al. .......................... 431/13 |

FOREIGN PATENT DOCUMENTS 1133733  11/1982  Canada .

*Primary Examiner*—Vit W. Miska
*Attorney, Agent, or Firm*—C. A. Rowley

[57] ABSTRACT

A low power consumption system for monitoring time of use of appliance incorporates a controller and a temperature sensor that is activated by the controller at intervals of X minutes to determine the temperature of the sensor. The sensed temperature is then compared with a threshold temperature and a counter is turned ON to accumulate time if the sensed temperature is at the desired level or turned OFF when the sensed temperature is not in the desired range. The counter remains in its ON or OFF position until the sensed temperature causes the counter to shift to the opposite position to the one it is in at that time. The counter receives oscillations from the oscillator which is continuously operating and only counts those oscillations when the counter is set in the ON position.

18 Claims, 3 Drawing Sheets

TIME MONITORING APPLIANCE

FIELD OF THE INVENTION

The present invention relates to a time monitoring appliance, more particularly, the present invention relates to a low power consuming time monitor particularly suited for application to a dental appliance or the like.

BACKGROUND OF THE INVENTION

The ability to monitor the time of use with appliances such as an oral appliance for orthodontics, sleep apnea or the like is extremely valuable information to the professional overseeing the work. Among the first to recognize this and provide a solution was Northcutt who in his U.S. Pat. No. 3,885,310 issued May 27, 1995, discloses such a system with the monitor mounted outside of the mouth in a restraining head band. The Northcutt system is activated, for example, by a suitable sensor sensing pressure, temperature, or a variety of other conditions that may be sensed when the device is in operation to trigger a timer to accumulate the time during which the sensor indicates that the system is in place, or complies to a condition, e. g., a condition indicating that the appliance is being worn is met. The system is covert in that the patient does not have access to the measured time as the timer must be read by an independent system that decodes the stored results.

Canadian patent 133733 issued Oct. 19, 1982 to Frohn (corresponding U.S. Pat. No. 4,255,138) discloses a monitoring system wherein the timer and a triggering switch are both positioned within the mouth cavity as part of the appliance. This system also uses a switch to turn the clock or timer ON when the condition sensed meets a set threshold indicating that the appliance is in position in the mouth, otherwise OFF.

An improvement the Frohn system is described in U.S. Pat. No. 5,245,592 issued Sep. 14, 1993 to Kuemmel et al. (assigned to Frohn). In this patent the timing oscillator frequency is measured when the recorder time of use is to be decoded (i.e. when the appliance is not in use) and this measured oscillator frequency provides a known frequency that is then used to obtain a more accurate determination of the time of use.

One of the major problems with these devices is available operating time for a given battery capacity as the power requirements are high, and the battery size, if the battery is to be part of the appliance and contained within the mouth cavity, must be relatively small.

BRIEF DESCRIPTION OF THE PRESENT INVENTION

It is an object of the present invention to provide a time monitoring system particularly suited for appliances such as dental appliances to permit monitoring of the time the appliance is in place and being used e.g. complies with a condition that is being monitored, preferably temperature.

Broadly, the present invention relates to an apparatus for monitoring time of use of an appliance comprising a timing oscillator means providing uniformly spaced time increment pulses, a controller, a sensor for sensing a condition indicating said appliance is in use, means for activating said sensor at spaced time intervals for increments of sufficient duration for said sensor to detect said condition, means for determining if said sensed condition is on one side of or another side of a selected threshold for said condition, a counter for counting said time increment pulses, means for setting said counter to an ON position if said sensed condition is on said one side of said threshold and to an OFF position when said sensed condition is on said other side of said threshold, said ON position activating said counter to accumulate said time increment pulses and record time of use until said means for setting is set to said OFF position and said OFF position preventing said counter from accumulating said time increment pulses until said means for setting sets said counter to said ON position.

Preferably said sensor will be a temperature sensor and said condition will be temperature and said one side of said threshold will be a temperature above said threshold.

Preferably, said time intervals will be at least 4 minutes.

Preferably, said temperature sensor will comprise a temperature dependent oscillator circuit having a temperature dependent resistor therein, said resistor changing resistance with change in temperature and adjusting the oscillation rate of said oscillator circuit in accordance with its resistance.

Preferably, said means to determine whether said sensed temperature is above or below said threshold temperature will include means for comparing oscillation rate of said oscillation circuit with a preset oscillation rate for said threshold temperature.

Preferably said system will further include an output system for reading said counter and for transmitting coded information indicating said time of use of said appliance.

Preferably, said output system will include means for connecting a separate source of power to said output system operating said output system.

Preferably said output system transmits a coded visual signal.

Preferably, said time intervals between which said means for activating said sensor will be of a selected time between 4 and 5 minutes.

Preferably, said sufficient time to determine temperature will be less than one second.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
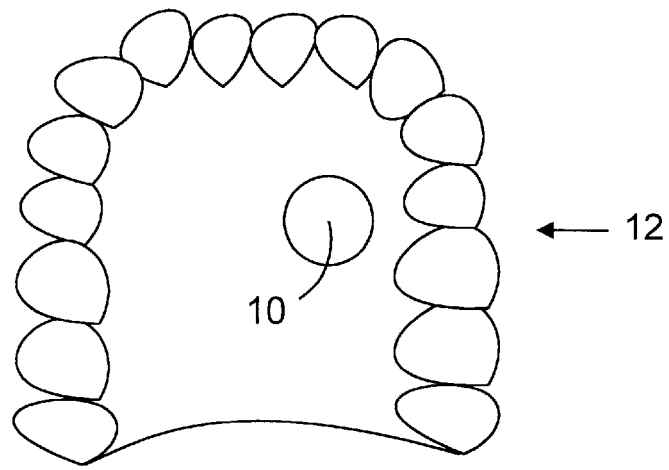
FIG. 1 is a plan view of an oral appliance incorporating the present invention.

As shown in FIG. 1, the present invention comprises a time monitor 10 mounted in any suitable manner on appliance 12, for example, it may be secured in a suitable cavity in the appliance 12 by means of a suitable adhesive such as an acrylic resin or be mechanically held in position, for example by stainless steel wires. It is preferred that removal by the user be difficult so that only the detal technician will normally remove it from the appliance 12

Figure 1A:
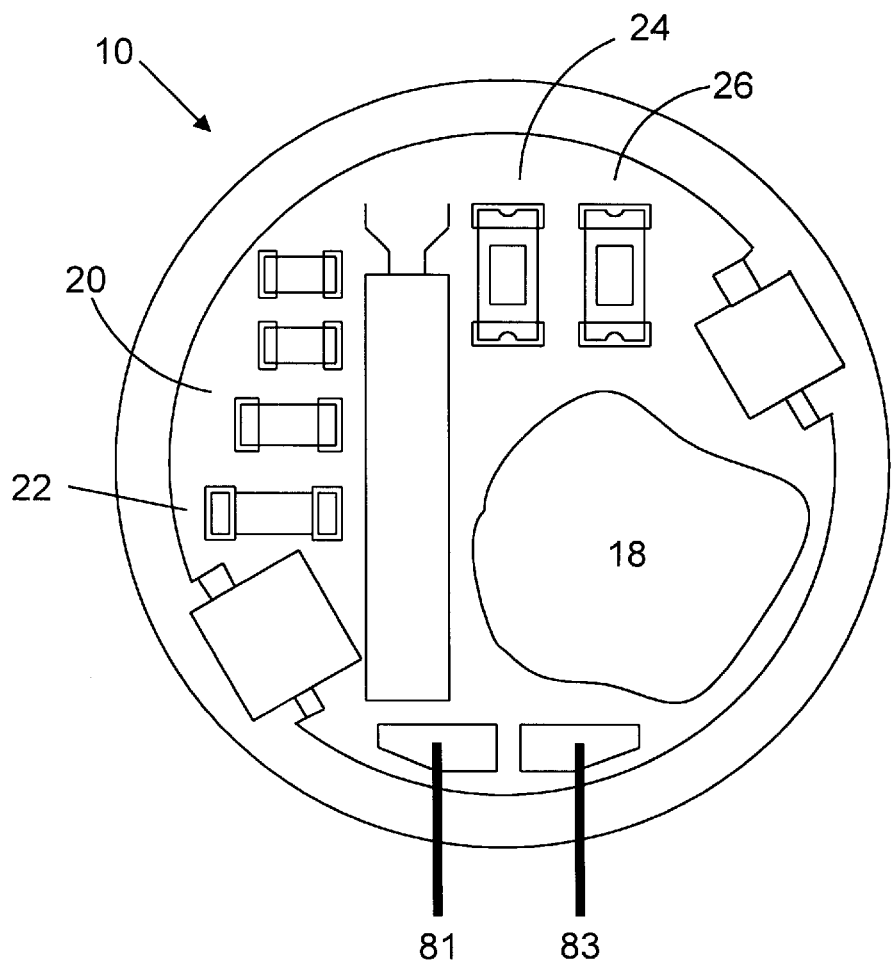
FIG. 1A is a schematic plan view of the monito of the present invention.

As shown in FIG. 1A a battery 14 providing the required power to the monitor 10 (described in more detail respectively in FIGS. 2 and 3) that incorporates an integrated circuit 18, thermistor 20 (part of the temperature sensor), and oscillator system 22 for providing uniformly timed pulses to provide the timing bases for the system only a portion of which is indicated. The oscillator system 22 functions to provide a stable series or sequence of uniformly spaced time increment pulses i.e. pulses at uniform intervals to provide a consistent base for defining time.

A preferred form of oscillator system 22 is described in "The High Performance Crystal Oscillator Circuits Theory and Application", Eric Vittoz et al., published in IEEE Journal of Solid State Circuits, Volume 23, No. 3, Jun. 1988.

Figure 2:
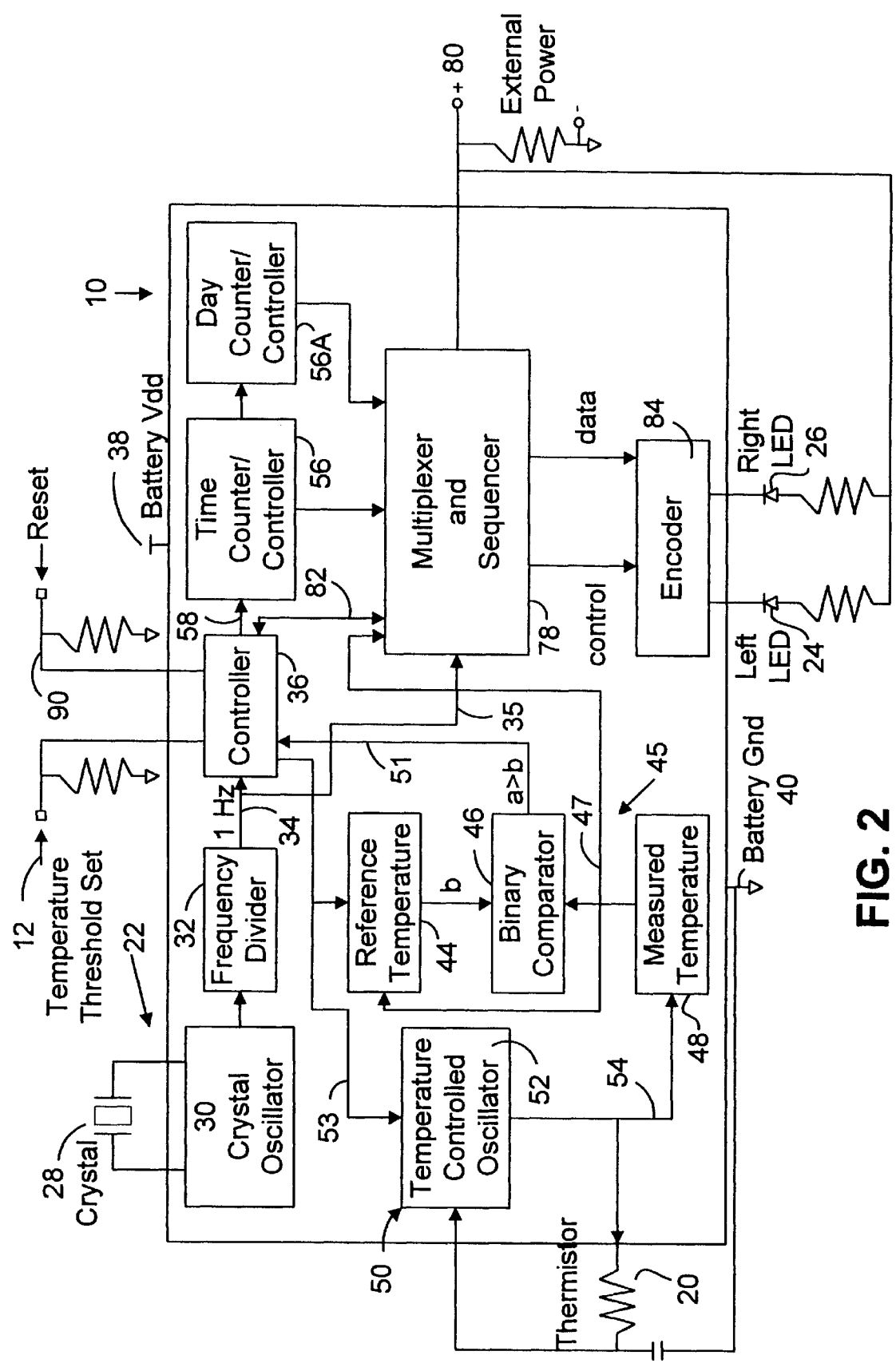
FIG. 2 is a schematic illustration of the overall system of the present invention.

As shown in FIG. 2, the oscillator system 22 for setting the time increments includes a high (preferably in the order of 10K Hz) frequency crystal 28 and a crystal oscillator circuit 30 the output of which is fed to a frequency divider 32, which preferably will have a low frequency output of for example, 1 Hz. The output of the divider 32 is fed as indicated at 34 to the control unit 36 of the time monitoring appliance 10 to provide the base time impulse to the controller 36.

As soon as the battery power from the battery 14 is connected as indicated by the terminals 38 and 40 in FIG. 2 the oscillator system 22 operates until the power of the battery 14 is depleted.

The temperature sensing oscillator circuit 50 includes the thermistor or temperature dependent resistor 20 that changes the operating frequency of the temperature dependent oscillator 52 in accordance with its resistance so that the temperature sensing oscillator circuit transmits a signal, the frequency of which is temperature dependent and corresponds with the temperature to which the resistor 20 is subjected, i.e. the ambient or surrounding temperature $T_A$. This signal which represents the frequency $F_S$ for the sensed temperature $T_A$ passes via line 54 to the measured or sensed temperature register 48 of the comparing system 45 composed or the register 48, the reference temperature register 44 and the comparator 46.

The controller 36 at spaced intervals sends a signal via line 53 that renders the temperature sensing system 50 operative for periods of time $O_T$ sufficient to sense the temperature. The intervals $P_T$ between the periods when the temperature sensor is operative will generally extend for a time $P_T$. Generally $P_T$ will be in the order of about 4 to 5 minutes, i.e. about 375*$O_T$ and normally $O_T$ requires will be less than about 1 second. The time interval $P_T$ between the temperature sensing periods is set by a specific count of time increment pulses from the system 22 by the controller 36 and preferably will correspond to a defined selected time $P_T$ of as above described of between about 4 and 5 minutes. It will be apparent that if the time is too long the accuracy of the timing system may be impaired and if too long the drain on the battery will be increased.

To operate the system, it is necessary to define a threshold temperature $T_H$ above which the monitor is set to an ON position so that the counter 56 will accumulate time. The selected threshold temperature $T_H$ will normally be slightly below normal body temperature e.g. 5° C. below body normal body temperature. The control 36 activates the counter 56 only over those time intervals $P_T$ when the ambient or surrounding temperature $T_A$ sensed by sensor 50 in the immediately preceding sensing operation $O_T$ is above the threshold temperature $T_H$ set in register 44 i.e. $T_A<T_H$. Thus the control 36 sets the counter 56 to an ON position only when the sensed temperature $T_A$ is above the threshold temperature $T_H$ and to an OFF position when the sensed temperature $T_H$ is below the threshold temperature $T_H$, i.e. $T_A>T_H$ as will be described further hereinbelow.

It will be apparent that a deadband may be provided between the ON and OFF positions i.e. to turn the counter 56 ON may be set so that temperature $T_A$ needs be several degrees higher than $T_H$ and/or to turn the counter 56 to an OFF position the temperature $T_A$ must be several degrees lower than $T_H$.

The threshold temperature $T_H$ is set as indicated at 42 by input to the controller 36 which then sets the reference count $F_H$ corresponding to the threshold temperature in the register 44. This reference temperature $T_H$ count $F_H$ (number of pulses in a selected time period i.e. frequency for the threshold temperature $T_H$) is compared in comparator 46 with the measured temperature $T_A$ count $F_S$ (number of pulses over a corresponding time period i.e. frequency for the measured temperature $T_A$) in register 48 and the information as to whether the reference or threshold temperature $T_H$ is higher than the measured temperature $T_A$ or vice versa is sent back to the controller 36 via the line 51.

It will be apparent that the referenced temperature $T_H$ is coded into the register 44 as a defined frequency $F_H$ which corresponds with the frequency of the circuit 50 incorporating the thermistor 20 when subjected to the selected threshold temperature. The comparator 46 thus simply determines whether the reference temperature is above or below the measured temperature by comparing the relative values of the reference frequency $F_H$ in register 44 with the frequency $F_S$ as generated by the temperature sensor 50 and applied to register 48 to indicate whether or not the sensed temperature $T_A$ is above or below the selected threshold $T_H$ and as above indicated, this information is fed to the controller 36.

Figure 3:
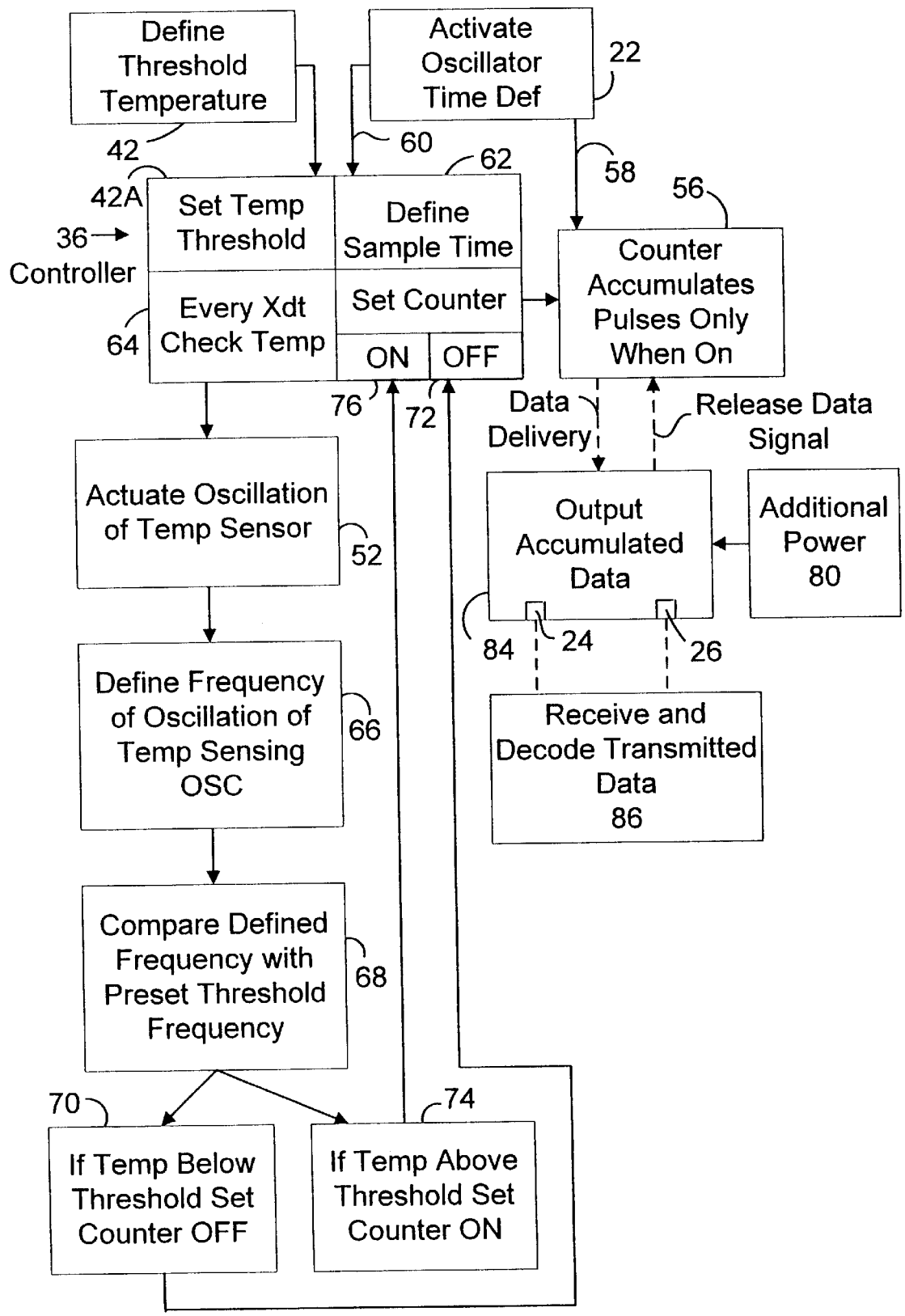
FIG. 3 is a flow diagram illustrating the operation of the present invention and its various components.

Thus, as shown in FIG. 3, once the temperature $T_H$ has been set as indicated at 42 and 42A in the controller 36 the temperature $T_H$ will normally not require further adjustment. However, if desired, it may be reset to a new threshold temperature.

The oscillator system 22 provides uniformly incremented time pulses to the controller 36 and to the counter 56 either directly as indicated by line 58 or via the control 34 as indicated by line 60. The controller 36 defines the sample time interval $P_T$ (time between actuation of the temperature sensing circuit 50) by counting time pulses as indicated at 62 and this sample time is then transmitted to the check temperature control 64 which every interval $P_T$, initiates an operation $O_T$ to check the temperature by temperature sensor 50. In the preferred embodiment of the present invention, the time interval $P_T$ or the time between temperature samples is 256 seconds, thus, every 256 seconds, the temperature sensing circuit 50 will be activated $O_T$ and the frequency $F_S$ of the oscillation for the temperature $T_A$ sensed will be defined as indicated at 66 and this information provided to the register 48 and compared with the frequency $F_H$ in the reference temperature register 44 as indicated at 68 in FIG. 3.

If the temperature $T_A$ sensed by sensor 50 is below the preset threshold temperature $T_H$ the counter 56 is set to OFF as indicated at 70 which triggers the set counter OFF 72 in the controller 34 which prevents the time increment pulses from being accumulated in the counter 56 until the set counter ON control 76 is activated as described below.

On the other hand, if the sensed temperature $T_A$ is above the threshold temperature $T_H$ then the set counter to ON control is activated as indicated at 74, this information is then fed to the set counter ON control 76 in the controller 34 which sets the counter 34 to accumulate time increment pulses from line 58. This continues until he set counter OFF control 72 is activated Since the temperature sensor 50 is only activated at spaced time intervals, i.e. very $P_T$ seconds, and remains ON for only sufficient time $O_T$ for the temperature to be sensed, it is apparent that the power consumption of the temperature sensor 50 is significantly reduced. Obviously some accuracy is lost in that once the set counter ON has been triggered, it will remain ON until the next temperature sensing sequence which as above indicated will be in the order of about 4 minutes and thus, one could accumulate 4 minutes time if one were to take the appliance to a non-use position e.g. out of the mouth, immediately after a set counter ON signal was received or in the reverse when the appliance is moved to operative position immediately after an set counter OFF signal is transmitted.

The above description relates to the preferred sensor namely a temperature sensor, another condition(s) indicating that the appliance is in use could be sensed in a similar manner with an appropriate sensor and used to set the ON and OFF conditions.

Referring back to FIG. 2, the counter 56 has been shown as further including a day counter 56A which will accumulate pulses when the time counter 56 counts pulses equivalent to X hours of uninterrupted use (X=4.5 hours has been found to be effective for some dental appliances, it may well be different for other applications).

It will be noted that an output system which includes the multiplexer and sequencer 78 is used to read the counter 56 (56A) and provide the required output data. This system permits covert operation in that the information contained in the counter 56 (56A) cannot be readily deciphered either by patient or attending physician, dentist and/or auxiliary without decoding.

As shown in FIGS. 2 and 3, the multiplexer 78 is activated by power from an external power source 80 applied via terminals 81 and 83 (see FIG. 1) so that it does not use power from the battery 14. When the outside power source 80 is connected, the controller 34 is activated as indicated by the line 82 to permit the counters 56 and 56A to feed data to the multiplexer sequence 78 which in turn feeds data to the encoder 84 that lights the left and right LED lights 24 and 26 in a specific sequence to indicate the number of days and the number of hours that the system has been active, i.e. time of ear of the appliance. These signals transmitted by controlled activation of the lights 24 and 26 are sensed and then decoded in a suitable decoder as indicated at 86 in FIG. 3.

The output from the multiplexer and sequencer 78 may include timing pulses delivered from line 34 via line 35 (see FIG. 2) and may also include the reference temperature $T_H$ delivered as indicated via line 47.

The system is reset by a signal may be sent as indicated at 90 to the controller 36 to reset the system.

The present invention thus provides an accurate measurement of time of use and requires very little power for its operation.

The illustrated arrangement permits the monitor 10 to be separated from the appliance 12 for connection to the external power source, if desired. It is possible to replace the monitor 10 in the appliance 12 with a second monitor 10 when the battery of the first monitor 10 is discharged. It is also possible to construct the monitor 10 so that a used or discharged battery 14 may be replaced with a new one when the monitor is removed from the appliance 12.

Having described the invention, modifications will be evident to those skilled in the art without departing from the scope of the invention as defined in the appended claims.

We claim:

1. An apparatus for monitoring time of use of an appliance comprising a battery powered integrated circuit having a continuously operating timing oscillator means providing uniformly spaced time increment pulses, a controller, a sensor for sensing a condition indicating said appliance is in use, means for recurrently activating said sensor after time intervals each composed of a preselected number of said time increment pulses, said means for recurrently activating said sensor activating said sensor for time increments each of sufficient duration for said sensor to detect said condition, means for determining if said sensed condition is on one side of or another side of a selected threshold for said condition, a counter for counting said time increment pulses, means for setting said counter to an ON position if said sensed condition is on said one side of said threshold and to an OFF position when said sensed condition is on said other side of said threshold, said ON position activating said counter to accumulate said time increment pulses continuously over succeeding of said time interval composed of a preselected number of said time increment pulses plus said time increment of sufficient duration for said sensor to detect said condition and record time of use based on counted number of said time increment pulses and thereby continue to accumulate said time increment pluses until said means for setting is set to said OFF position when said sensed condition is on said other side of said threshold and said OFF position activating means for preventing said counter from accumulating said time increment pulses until said means for setting sets said counter to said ON position.

2. An apparatus for monitoring time of use as defined in claim 1 wherein said sensor is a temperature sensor, said threshold is a selected threshold temperature and said condition is temperature and said one side of said threshold is a temperature above said threshold temperature.

3. An apparatus for monitoring time of use as defined in claim 2 wherein said time intervals between which said means for activating said temperature sensor have a duration of between 4 and 5 minutes.

4. An apparatus for monitoring time of use as defined in claim 2 wherein said temperature sensor comprises a temperature dependent oscillator circuit having a temperature dependent resistor therein, said resistor changing resistance with change in temperature and adjusting oscillation rate of said oscillator circuit in accordance with its resistance.

5. An apparatus for monitoring time of use as defined in claim 3 wherein said temperature sensor comprises a temperature dependent oscillator circuit having a temperature dependent resistor therein, said resistor changing resistance with change in temperature and adjusting oscillation rate of said oscillator circuit in accordance with its resistance.

6. An apparatus for monitoring time of use as defined in claim 4 wherein said means to determine whether said sensed temperature is above or below said threshold temperature includes means for comparing oscillation rate of said oscillation circuit with a preset oscillation rate for said threshold temperature.

7. An apparatus for monitoring time of use as defined in claim 5 wherein said means to determine whether said sensed temperature is above or below said threshold temperature includes means for comparing oscillation rate of said oscillation circuit with a preset oscillation rate for said threshold temperature.

8. An apparatus for monitoring time of use as defined in claim 1 wherein further including an output system for reading said counter and for transmitting coded information indicating said time of use of said appliance.

9. An apparatus for monitoring time of use as defined in claim 8 wherein said output system includes means for connecting a separate source of power to said output system operating said output system.

10. An apparatus for monitoring time of use as defined in claim 9 wherein said output system transmits a coded visual signal.

11. An apparatus for monitoring time of use as defined in claim 2 wherein further including an output system for reading said counter and for transmitting coded information indicating said time of use of said appliance.

12. An apparatus for monitoring time of use as defined in claim 11 wherein said output system includes means for connecting a separate source of power to said output system operating said output system.

13. An apparatus for monitoring time of use as defined in claim 12 wherein said output system transmits a coded visual signal.

14. An apparatus for monitoring time of use as defined in claim 4 wherein further including an output system for reading said counter and for transmitting coded information indicating said time of use of said appliance.

15. An apparatus for monitoring time of use as defined in claim 14 wherein said output system includes means for connecting a separate source of power to said output system operating said output system.

16. An apparatus for monitoring time of use as defined in claim 15 wherein said output system transmits a coded visual signal.

17. An apparatus for monitoring time of use as defined in claim 3 wherein further including an output system for reading said counter and for transmitting coded information indicating said time of use of said appliance, said output system including means for connecting a separate source of power to said output system operating said output system and said output system transmits a coded visual signal.

18. An apparatus for monitoring time of use as defined in claim 5 wherein further including an output system for reading said counter and for transmitting coded information indicating said time of use of said appliance, said output system including means for connecting a separate source of power to said output system operating said output system and said output system transmits a coded visual signal.

* * * * *